US008452436B2

(12) United States Patent
Pattijn et al.

(10) Patent No.: US 8,452,436 B2
(45) Date of Patent: May 28, 2013

(54) TOOTH MOVEMENT SYSTEM AND METHOD

(75) Inventors: Veerle Pattijn, Kersbeek-Miskom (BE); Bert Van Roie, Leuven (BE); Carl Van Lierde, Meerbeke (BE)

(73) Assignee: Materialise Dental N.V., Leuven (BE)

( * ) Notice: Subject to any disclaimer, the term of this patent is extended or adjusted under 35 U.S.C. 154(b) by 369 days.

(21) Appl. No.: 12/809,904

(22) PCT Filed: Dec. 22, 2008

(86) PCT No.: PCT/EP2008/068191
§ 371 (c)(1),
(2), (4) Date: Jun. 21, 2010

(87) PCT Pub. No.: WO2009/080815
PCT Pub. Date: Jul. 2, 2009

(65) Prior Publication Data
US 2010/0280798 A1 Nov. 4, 2010

(30) Foreign Application Priority Data
Dec. 21, 2007 (GB) .................................. 0724992.3

(51) Int. Cl.
G06F 19/00 (2006.01)
A61C 7/00 (2006.01)
(52) U.S. Cl.
CPC ..................................... A61C 7/002 (2013.01)
USPC ................................................ 700/98; 433/8

(58) Field of Classification Search
CPC .................................. A61C 7/00; A61C 7/002
USPC ............... 700/98; 433/24, 8, 29, 213; 703/1, 703/11
See application file for complete search history.

(56) References Cited

U.S. PATENT DOCUMENTS

| | | | |
|---|---|---|---|
| 5,431,562 A * | 7/1995 | Andreiko et al. ............... | 433/24 |
| 6,068,482 A | 5/2000 | Snow | |
| 6,616,444 B2 * | 9/2003 | Andreiko et al. ................. | 433/3 |
| 6,736,638 B1 | 5/2004 | Sachdeva et al. | |
| 7,160,107 B2 * | 1/2007 | Kopelman et al. .............. | 433/24 |
| 7,273,368 B2 * | 9/2007 | Taub et al. ...................... | 433/24 |
| 7,291,011 B2 * | 11/2007 | Stark et al. ..................... | 433/24 |
| 7,296,996 B2 * | 11/2007 | Sachdeva et al. ............... | 433/24 |
| 7,422,430 B2 * | 9/2008 | Sachdeva et al. ............... | 433/24 |
| 7,869,983 B2 * | 1/2011 | Raby et al. ........................ | 703/2 |
| 7,993,133 B2 * | 8/2011 | Cinader et al. .................. | 433/24 |

(Continued)

FOREIGN PATENT DOCUMENTS
WO   WO 03/026527    4/2003

OTHER PUBLICATIONS

International Preliminary Report on Patentability (PCT/EP2008/068191), completed Dec. 28, 2009.
International Search Report (PCT/EP2008/068191), mailed Apr. 3, 2009.

(Continued)

*Primary Examiner* — Dave Robertson
(74) *Attorney, Agent, or Firm* — Clark & Elbing LLP

(57) ABSTRACT

The invention features computer based methods and systems for obtaining information about tooth movement caused by at least one orthodontic element fixed on a dentition. The invention also features computer programs for generating, when executed, a method for obtaining information about tooth movement caused by at least one orthodontic element fixed on a dentition, as well as non-transitory machine readable storage media containing such computer programs.

19 Claims, 3 Drawing Sheets

U.S. PATENT DOCUMENTS

| | | | |
|---|---|---|---|
| 7,993,134 B2 * | 8/2011 | Wen | 433/24 |
| 8,142,187 B2 * | 3/2012 | Sporbert et al. | 433/24 |
| 8,192,197 B2 * | 6/2012 | Sporbert et al. | 433/24 |
| 2003/0059736 A1 | 3/2003 | Lai et al. | |
| 2004/0161722 A1 | 8/2004 | Lai et al. | |
| 2005/0079468 A1 | 4/2005 | Chishti et al. | |
| 2006/0275736 A1 * | 12/2006 | Wen et al. | 433/213 |
| 2008/0182221 A1 | 7/2008 | Chishti et al. | |
| 2008/0311535 A1 * | 12/2008 | Andreiko | 433/24 |

OTHER PUBLICATIONS

Rodrigues et al., "An Interactive Simulation System for Training and Treatment Planning in Orthodontics," *Computers and Graphics* 31(5): 688-697 (2007).

Written Opinion of the International Searching Authority (PCT/EP2008/068191), mailed Apr. 3, 2009.

Response to the Written Opinion (PCT/EP2008/068191), dated Oct. 21, 2009.

\* cited by examiner

TOOTH MOVEMENT SYSTEM AND METHOD

CROSS-REFERENCE TO RELATED APPLICATIONS

This application is the U.S. National Stage of International Application No. PCT/EP2008/068191, filed on Dec. 22, 2008, which claims priority to British patent application no. 0724992.3, filed on Dec. 21, 2007.

FIELD OF THE INVENTION

The invention is related to the field of dentistry, more particular orthodontics. Three-dimensional digital imaging technology (CT, μCT, optical scanning . . . ) is ever more frequently used by the dentist to analyze the patient's dentition and to determine the orthodontic treatment plan and simulate the intervention in advance. The current invention describes the use of 3D imaging techniques and computer technology to simulate and predict tooth movement as a function of the chosen treatment, i.e. a specific orthodontic appliance. In this way treatment options can be compared and the most optimal (shortest treatment time, lowest forces . . . ) treatment for each individual patient can be selected.

BACKGROUND TO THE INVENTION

Orthodontic treatment is characterized by applying forces to individual teeth aimed at moving them to a desired position. To induce tooth movement efficiently, the forces applied on the teeth should be within a certain range: too high forces result in slow, nonexistent or pain-full tooth movement, while too low forces result in slow or nonexistent tooth movement. Thus, the orthodontic removable or fixed appliances should induce forces on the teeth within the desired range.

To apply forces on the teeth using fixed appliances, i.e. orthodontic bands or brackets and archwires, two methods are generally used: either the standard edgewise technique or the straight-wire technique.

The standard edgewise technique uses brackets with their slot at right angles relative to the tooth axis and bends made in the archwire. The type of bends ($1^{st}$, $2^{nd}$, $3^{rd}$ order bends) determine the forces applied to the teeth and the resulting tooth movement.

The straight-wire technique uses fully programmed brackets (varying base thickness and varying mesio-distal angulation and/or bucco-lingual inclination of slot relative to base) varying for each individual tooth and a "straight" archwire. Forces are induced by the deformation of the wire (with respect to its initial unloaded shape) applied to position and hold it into the brackets fixed on the patient's teeth. If the induced forces are within the desired range the tooth will move. As the tooth moves, the deformation of the wire reduces and the forces delivered on the teeth diminish. Once the force decreases below the threshold value for inducing tooth movement, the tooth movement will stop. Therefore during treatment different wires, having different stiffnesses (which are determined by the cross-section and the material properties [Young's modulus] of the wire) are used. Typically, at the beginning of the orthodontic treatment the wire will have a low stiffness, allowing high deformations of the wire without inducing too high forces on the teeth. The succeeding wires in the orthodontic treatment will have always a higher stiffness since forces within the specified range for tooth movement must be induced at smaller and smaller deformations.

Both types of orthodontic treatment are characterized by periodic (every four to eight weeks) meetings of the patient with the dentist/orthodontist, during which the induced tooth movements are verified and the treatment is adjusted if needed. This means that brackets may need repositioning, arch wires may need to be changed. The total treatment typically lasts one and a half up to two years, but the final treatment time is not well predictable in advance. Therefore it would be desirable to be able to simulate treatment options in advance and estimate the total treatment time in order to determine the optimal treatment.

More recently, digitalization and 3D computer planning has been introduced in the orthodontic practice. The traditional plaster models of the patient's dentition are replaced by a digital surface representation of the patient's dentition, visualized with dedicated software. These software applications typically also allow performing tooth measurements (mesio-distal width, vestibulo-lingual width, tooth height, interproximal contacts . . . ) and orthodontic analyses (symmetry, Bolton, Korkhaus, occlusal contacts . . . ). More advanced software applications allow segmentation and further repositioning of the individual teeth, positioning virtual brackets . . .

Patent application US 2005/0079468 A1 describes a method for dividing an orthodontic treatment path (from initial tooth position to desired tooth position) into clinically appropriate sub steps for repositioning the teeth of a patient. A digital finite element model is made of the patient's teeth and related mouth tissue and of the shape and material of each of a sequence of appliances to compute the actual effect of the designed appliances on the tooth movement. The resulting tooth movements are verified against clinical constraints and if needed appliances and sub steps are adapted. Finally all appliances needed for the orthodontic treatment (reposition teeth in steps as defined and verified during finite element computations) are manufactured.

SUMMARY OF THE INVENTION

The present invention has an object to analyze a patient's dentition and to determine an orthodontic treatment plan by simulating an intervention in advance. The current invention describes the use of 3D imaging techniques and computer technology to simulate and predict tooth movement as a function of the chosen treatment, i.e. a specific orthodontic appliance. In this way treatment options can be compared and the most optimal (shortest treatment time, lowest forces . . . ) treatment for each individual patient can be selected.

The current invention differs from above-mentioned prior art in the sense that the sub-steps of the tooth movement are not predefined but computed based on a simulation of brackets and wire as they would be used in the orthodontic treatment of the patient. This means that the sub-steps are calculated based on the relationship between the applied loads and the tooth movement; only one of both parameters can be chosen freely. Thus, either the tooth load is specified and applied in order to calculate the resulting tooth movement or vice versa the tooth movement is specified and applied in order to calculate the tooth load that should be applied. Moreover, the current invention allows predicting the time at which brackets and/or archwire should be changed, and comparing different treatment options with respect to tooth loading and duration.

The present invention provides, systems, methods and software as defined in the attached claims and explained in the attached description with reference to the drawings.

BRIEF DESCRIPTION OF THE DRAWINGS

Embodiments of the invention will be described, by way of example only, with reference to the accompanying drawings in which.

DESCRIPTION OF PREFERRED EMBODIMENTS

Figure 1:
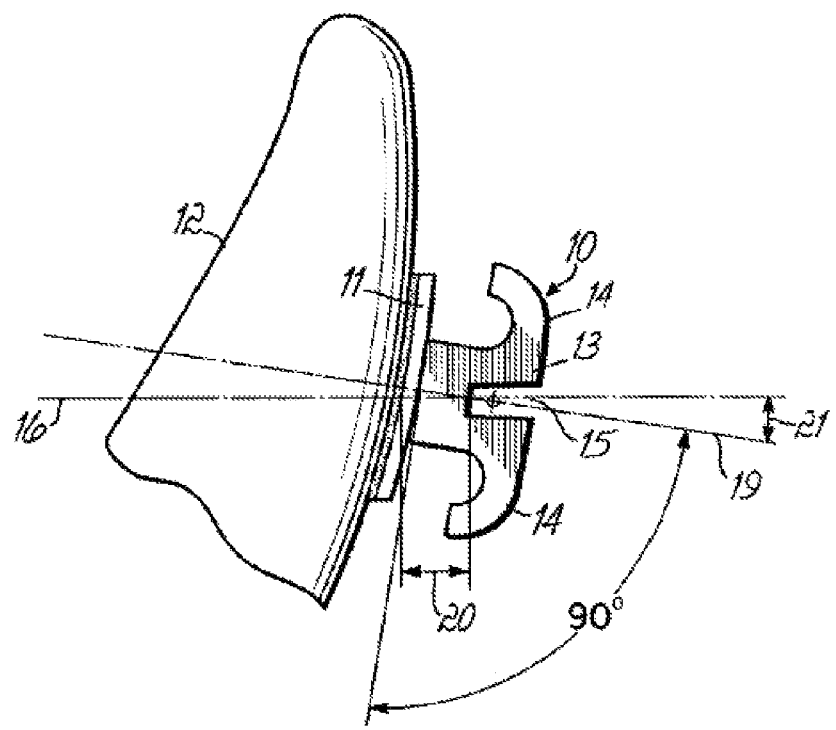
FIG. 1 shows a bracket applied to a tooth as shown in FIG. 1 of US2003/0224317.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practised without these specific details. In other instances, well-known methods, structures and techniques have not been shown in detail in order not to obscure an understanding of this description.

The invention will now be described by a detailed description of several embodiments of the invention. It is clear that other embodiments of the invention can be configured according to the knowledge of persons skilled in the art without departing from the true spirit or technical teaching of the invention, the invention being limited only by the terms of the appended claims.

The current invention provides a method and computer based system to either optimize orthodontic treatment or compare different orthodontic treatments, using as input the initial and desired (planned) tooth positions. The parameters to be optimized or compared are either the treatment time or the applied tooth loads.

FIG. 1 shows an orthodontic element such as a bracket applied to a tooth to which an archwire is attached as known from US2003/0224317. Orthodontic elements, such as brackets, are typically glued onto the non-visible lingual faces of the teeth. Patent application US2003/0224317 A1 states that its objective is to reduce chair time for the orthodontist and treatment time for the patient by providing the features of custom orthodontic treatment designed in a way that serves the objectives of custom appliances, making their advantages available to a degree, at least, to patients at a proportionately lower cost. The present invention differentiates itself from the above-mentioned patent application in the sense that in the present invention a time simulation of a selected orthodontic treatment can be performed, i.e. the treatment time can be calculated as well as the points of time at which the archwire must be changed to make sure that the tooth loads remain in the range inducing tooth movement. In the above-mentioned patent application no reference is made on how the invention will result in a reduction of the treatment time and how large this reduction will be. The following steps describe embodiments of the present invention in more detail. A flow diagram showing method 100 in accordance with an embodiment of the present invention is shown in FIG. 3.

Figure 3:
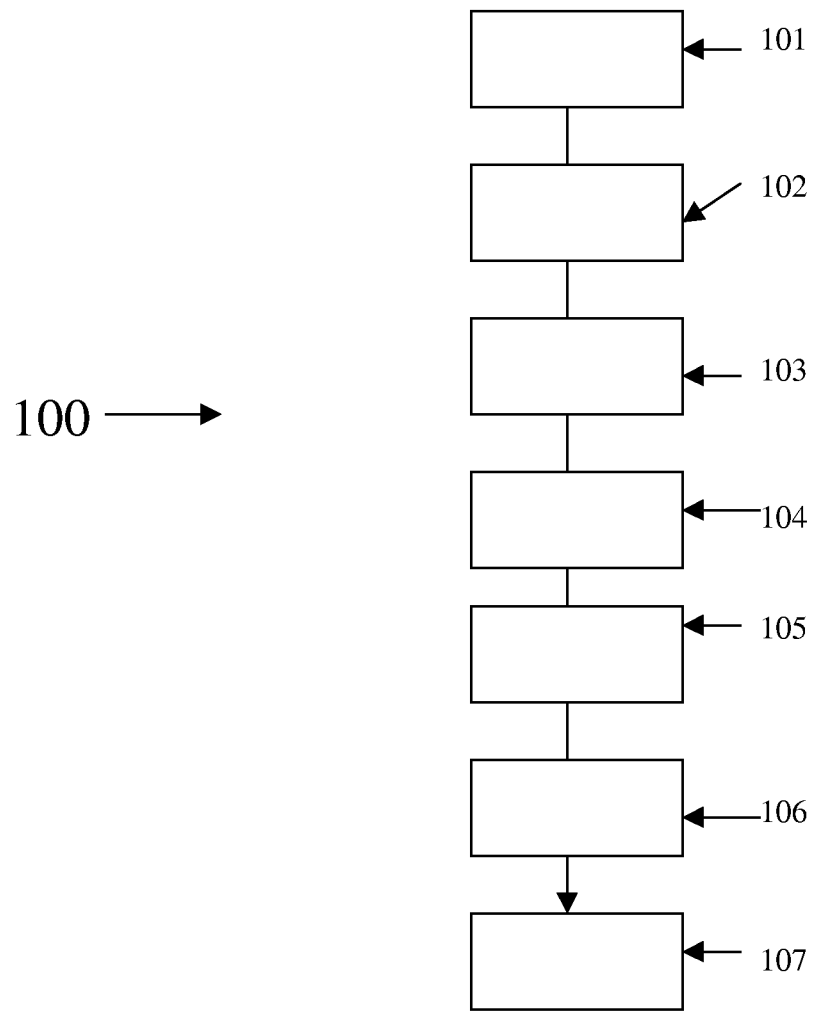
FIG. 3 is a flow diagram of an embodiment of the present invention.

1) Acquisition of information related to the patient's current dentition (step 101 FIG. 3).

At first the patient's dentition is digitized either directly or indirectly. Therefore different measurement techniques are available: intra-oral scanning (direct method), μCT scanning of impressions, μCT or optically scanning of plaster casts poured from the impressions, etc. The result of the above-mentioned digitization techniques is in general (but not limited to) either a point cloud or a triangulated mesh description of the patient's dentition. In the former case software exist to convert the point cloud into a surface description (e.g. triangulated mesh). The first step will result in a surface description of the patient's dentition, referred to as digital cast.

Besides digitizing the crowns of the patient's teeth, also information of the shape of the roots of the patient's teeth can be obtained. Therefore medical imaging techniques which can generate 2D or volumetric images like X-rays, CT or Cone Beam CT scan, MRI scan, can be used. These imaging techniques result in grey-value images of the bone, teeth and surrounding tissues.

Based on standard X-rays images (projection images) 2D dimensions of the roots can be obtained and used to personalize a generic tooth root model, which can be defined for each type of tooth. Based on CT or MRI images, 3D surface models of the full teeth (crown and root) can be obtained by using segmentation techniques of commercially available software packages (e.g. SimPlant, Materialise Dental NV).

In a next step the root models are combined with the digital cast, using registration and/or morphing techniques.

2) Determination of individual teeth and their type (step 102 FIG. 3).

In a second step the individual teeth are determined from the digital cast. Therefore different techniques (manual, semi-automatic, or fully automatic) exist and some are described in patent application WO 2007/009719 A1 (Method for (semi-) automatic dental implant planning) which is incorporated herein in its entirety. Patent application U.S. Pat. No. 7,063,532 B1 (Subdividing a digital dentition model) also describes computer automated techniques for subdividing, or segmenting, a digital dentition model into models of individual dentition components, including tooth crowns, tooth roots, and gingival regions and is incorporated herein in its entirety.

Once the individual teeth are available as separate entities, the type of each tooth is determined, i.e. incisor, canine, premolar, or molar. The user can be asked to specify the tooth types or procedures based on feature recognition can be used for an automated identification of the tooth type.

3) Identification of tooth axes and reference point (step 103 FIG. 3).

Once individual teeth and their type are known, tooth axes (long axis, bucco-lingual axis, mesio-distal axis) are determined as well as a reference point on the tooth surface. The tooth axes will allow determining angulation and inclination angle values for each tooth. In general, the FA point (Facial Axis point, i.e. the point on the facial axis that separates the gingival half of the crown from the occlusal half) is used as the reference point, and refers to the point in which the bracket is positioned. In case of lingual bracket positioning another point will be identified as the reference point on the tooth surface.

4) Creation of desired tooth setup (step 104 FIG. 3).

The desired tooth set-up (including position and orientation of each individual tooth) can be obtained by creating a digital 3D representation of the desired tooth position either using computer software to reposition the digital 3D models of the individual teeth (manual, semi-automatic, or fully automatic) or digitizing a physical model representing the new tooth setup as made by a dental technician. In the latter case, the individual teeth must be determined again as separate entities using the routines as described in step 2.

5) Bracket selection and positioning (step 105 FIG. 3).

Based on initial and final tooth positions the brackets are selected and positioned virtually onto the teeth. This can be carried out automatically, semi-automatically or manually. When using the straight-wire technique the fully programmed brackets (pre-angulated, pre-torqued, and built-in offsets and insets to accommodate differences in morphology of various types of teeth) should be virtually positioned on the individual teeth in such a way that when teeth are in their desired (planned) position all the slots of the brackets are aligned to the un-deformed archwire. This condition determines the orientation of the slots of the brackets relative to the individual teeth. Based on the angulation and inclination of each individual tooth in the desired position, the desired angulation and inclination angle that must be built-in in the fully programmed bracket is determined, to ensure a good contact between the base of the bracket and the tooth surface. Either custom brackets may be designed or commercially available fully programmed brackets are selected that correspond as good as possible with the optimal solution. Patent application US2003/0224317 A1 describes different methods for deriving geometric parameters of an appliance suitable for the individual patient based upon which an orthodontic appliance is selected from standard or custom appliance components or a combination of both. Now the selected brackets (a digital library of these brackets should be available) are virtually positioned onto the teeth in their desired orientation and as close as possible to the FA point. The transformation needed to go from desired tooth position to initial tooth position is computed and applied to the corresponding bracket, resulting in the position of the bracket on the tooth in its initial position.

The type of bracket (e.g. standard versus self-ligating) in combination with the type of archwire determines the load applied to the individual tooth. For standard and self-ligating brackets, friction forces are determined by the cross-section of the archwire and the type of ligature. The type of cross-section of the archwire (round versus rectangular) determines whether or not torque (around the long axis of the archwire) loads can be induced.

6) Computing tooth loads and resulting movement (step 106 FIG. 3).

General methods of predicting tooth movement under load are known to the skilled person, see for instance, "Modern Computational Methods, by Herbert A. Koenig, published by Taylor & Francis, 1998, chapter 14-3, "Prediction of tooth movements". As one starting point to estimate the applied force and tooth movement, a mathematical modeling can be performed by evaluating all individual data on tooth movement, e.g. from known cases. A nonlinear regression analysis of these data provides an equation to describe the characteristics of the relation between force magnitude and the rate of tooth movement. By use of regression, the power of the analysis is increased because problems with small sample size and a large interindividual variation are circumvented. Such a model can identify a range of forces and velocity of tooth movement produced.

Figures 2A, 2B:
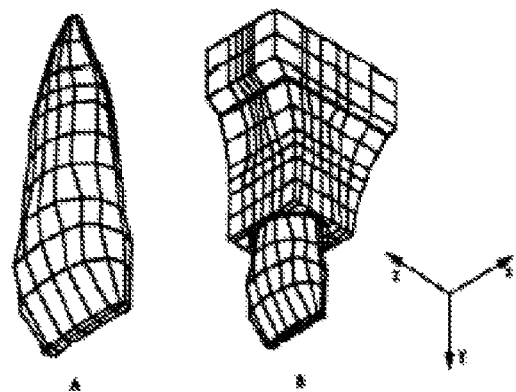
FIGS. 2a and b are schematic representation of a) a finite element representation of a PLD, b) a finite element representation of a tooth and bone set.

An alternative method is biomechanical modeling. The movement of teeth is not a simple deformation process. A tooth is surrounded by a membrane known as the periodontal ligament (PDL). When the PDL is stressed a growth process begins which allows the tooth to move much further than by simple bending strain. Biomechanical stress and/or strain in the periodontal ligament can be used to predict tooth movement. The finite element method (FEM) can be used for stress analysis in biological systems, where local stress and/or strain cannot be measured directly in a nondestructive manner. FIGS. 2a and b are schematic representation of a) a finite element representation of a PLD, b) a finite element representation of a tooth and bone set as shown and described in the book by Koenig. Finite element analysis provides accurate modeling of the tooth-periodontium system with its complicated 3-dimensional geometry. Different material models, i.e. a viscoelastic material model or a poroelastic model, have been proposed for analyzing the mechanical properties of the PDL, see Kuijpers-Jagtman Van Driel W D, Leeuwen E J, Von den Hoff J W, Maltha J C. "Time-dependent mechanical behavior of the periodontal ligament." Proc Instn Mech Engrs. 2000; 214:497-504, Tanne K, Yoshida S, Kawata T, Sasaki A, Knox J, Jones M L. "An evaluation of the biomechanical response of the tooth and periodontium to orthodontic forces in adolescent and adult subjects." Br J Orthod. 1998; 25:109-115, Andersen K L, Pedersen E H, Melsen B. "Material parameters and stress profiles within the periodontal ligament." Am J Orthod Dentofacial Orthop. 1991; 99:427-440.

In a preferred embodiment an analytical model simulating the straight-wire technique is used for modelling the archwire and brackets to compute the forces and torques applied onto the individual teeth in accordance with the present invention. These computed forces and torques serve as input for a second analytical model representing the teeth and their periodontal ligament, which is used for computing the induced tooth movements. Applying these tooth movements, results in a new position of the teeth and brackets. In this new position it should be verified whether or not teeth (crowns or roots) are making contact with or even penetrating neighbouring teeth. In the former case contact forces between neighbouring teeth must be computed and taking into account as additional tooth load (besides load applied by bracket) when computing the next tooth movement step. In the latter case the tooth movement should be limited until contact, which will bring us to the former case. The process of calculating forces and torques applied by the archwire, followed by calculating induced tooth movements, is repeated until the desired (planned) tooth positions are obtained.

When during this process, tooth movement is no longer induced by the applied loads, the archwire should be replaced by a stiffer archwire and calculations should be restarted using the new archwire specifications.

Since during the calculation process the time is tracked as well, it will be possible to determine the total treatment time as well as the points of time at which the archwire must be replaced with the next one.

The analytical model for computing loads (forces and torques) applied on the individual teeth through the archwire and brackets is based on two principles: (1) the principle of reciprocity and (2) the third Newtonian axiom.

The principle of reciprocity refers to the fact that the archwires used for the orthodontic treatment always want to return to their initial un-deformed shape. This is realised by limiting the deformation of the archwires to fully elastic deformation (i.e. fully reversible deformation) and not allowing permanent deformation. The yield point of the archwire indicates the maximum amount of stress that the archwire can endure without becoming permanently deformed. Therefore the forces applied to the archwire must be limited to keep the maximum stress in the archwire below the yield point, or another archwire (cross-section, material properties) should be selected.

Based on the third Newtonian axiom (stating the equivalence of acting and reacting forces) one can state that since the brackets are rigidly connected to the teeth the loads applied by the brackets on the teeth are equal to the loads applied by the archwire onto the brackets. Furthermore the latter loads are equal but opposite of the loads applied by the brackets onto the archwire, which are the loads needed to deform the archwire and hold it into the brackets.

The analytical model which is based on the stiffness method, represents the initial archwire shape and individual bracket positions, and is used to compute the loads needed to deform the archwire and hold it into the brackets. This model exists of a finite number of elements representing the archwire in its initial shape, i.e. its un-deformed shape that occurs when no forces are applied onto it. The material properties, the cross-section, and the shape of the archwire are parameters in the analytical model, so that each archwire can be modelled.

At first the un-deformed wire is positioned as close as possible to the brackets as positioned onto the teeth in their initial position. Then for each bracket the point of the archwire closest to the bracket is determined. These points of the archwire are obliged to move into their nearest bracket and the required forces and torques are calculated, as well as the global deformation of the archwire. In a next step the magnitude of the force applied tangentially on the archwire is verified. If this force does not exceed the maximal friction force that can be generated between bracket and archwire, then the solution is plausible. Else the tangential force is limited to the maximal friction force and the resulting tangential displacement is calculated. If this displacement is smaller than half the width of the bracket this new solution is plausible. Else a new point of the archwire must be selected to be moved into the bracket and the calculation restarts at the beginning and is repeated until a plausible solution is found.

The second analytical model representing tooth and periodontal ligament (PDL) requires as input the 3D shape of the tooth (i.e. crown and root), the bone level, and the load (forces and torques) applied on the tooth, and gives as output the tooth movement in time. The model starts by making a 3D model of the PDL, based on the 3D information of the tooth roots. For reasons of simplicity the PDL may be modelled as a 3D paraboloid or a 3D elliptical paraboloid for teeth with one root. The PDL is characterized by its thickness, Young's modulus, and Poisson coefficient. The bone surrounding the tooth is characterized by two viscosity coefficients, i.e. functions describing the bone remodelling in response to hydrostatic and deviatoric stresses.

These viscosity coefficients may be adapted in function of the quality of the bone surrounding the tooth. The model is used to calculate first the stresses in the PDL based on the tooth load, second the resulting bone remodelling, and third the resulting tooth movement, and this iteratively for small time steps (typically one day).

The extension of the above-described analytical model to teeth with multiple roots could be done in two ways: (1) defining an equivalent one root model for the multiple roots or (2) modelling each root as a 3D (elliptical) paraboloid. In the latter case the model used for calculating the tooth movement in function of the applied load should be adapted as well. First the load on each individual root must be estimated. Using these loads the bone remodelling can be computed around each root using the model for single rooted teeth, as well as the resulting tooth displacement. If these separately calculated tooth displacements are unequal the load distribution should be adapted and the calculation of the displacements restarted. This process is repeated until displacements are equal.

Simulation of the tooth movements has the advantage that a validation evaluation of the treatment can be performed in advance. It can be verified whether or not the tooth roots penetrate through the bone or if teeth collide during treatment. If collisions or penetrations do occur the treatment can be changed and a new simulation can be performed. Also stripping and extraction of teeth can be simulated in advance.

7) The above-described models can be used in different ways (step 107 FIG. 3), each of which is an embodiment of the present invention.
   (1) Starting from initial tooth position, bracket position and archwire shape, the tooth loads (forces and torques) are calculated and then used as input for determining the tooth movement in time.
   (2) The influence of different archwires (global shape, cross-section, material properties) on the tooth loads, the induced tooth movement, and the total treatment time can be calculated. Based upon this, the optimal (in function of treatment time, or tooth loads . . . ) succession of archwire types can be determined.
   (3) The desired tooth movement is used as input to calculate necessary tooth loading (forces and torques), which can then be used to determine bracket positions and/or archwire shape(s).
   (4) Applicable for bent wires
   (5) Select position of reference point (for fixing bracket) to optimize treatment time, tooth loading . . .
   (6) Determine tooth movement to avoid tooth contact.

Figure 4:
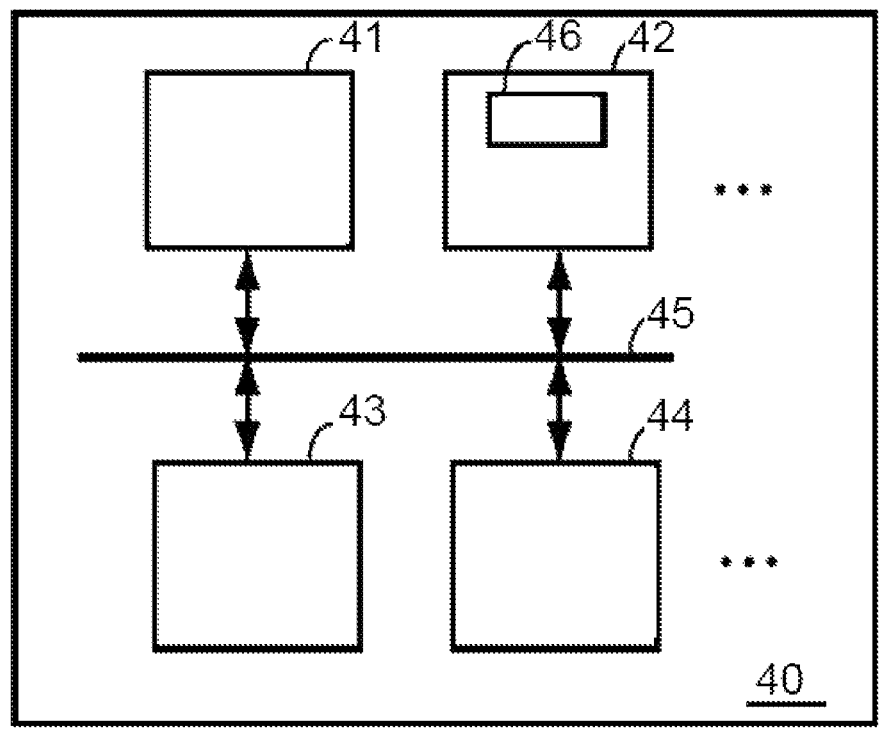
FIG. 4 is a schematic representation of a computer system that can be used with the present invention.

As indicated above the present invention also provides a processor system for use in dental planning. The processing system may include a computing device or processing engine, e.g. a microprocessor. Any of the methods described above according to embodiments of the present invention or claimed may be implemented in a processing system 40 such as shown in FIG. 4. FIG. 4 shows one configuration of processing system 40 that includes at least one customisable or programmable processor 41 coupled to a memory subsystem 42 that includes at least one form of memory, e.g., RAM, ROM, and so forth. It is to be noted that the processor 41 or processors may be a general purpose, or a special purpose processor, and may be for inclusion in a device, e.g. a chip that has other components that perform other functions. Thus, one or more aspects of the method according to embodiments of the present invention can be implemented in digital electronic circuitry, or in computer hardware, firmware, software, or in combinations of them. The processing system may include a storage subsystem 43 that has at least one disk drive and/or CD-ROM drive and/or DVD drive. In some implementations, a display system, a keyboard, and a pointing device may be included as part of a user interface subsystem 44 to provide for a user to manually input information, such as parameter values. Ports for inputting and outputting data, e.g. related to the planning also may be included. More elements such as network connections, interfaces to various devices, and so forth, may be included, but are not illustrated in FIG. 4. The various elements of the processing system 40 may be coupled in various ways, including via a bus subsystem 45 shown in FIG. 4 for simplicity as a single bus, but which will be understood to those in the art to include a system of at least one bus. The memory of the memory subsystem 42 may at some time hold part or all (in either case shown as 46) of a set of instructions that when executed on the processing system 40 implement the steps of the method embodiments described herein.

The present invention also includes a computer program product which provides the functionality of any of the methods according to the present invention when executed on a computing device. Such computer program product can be tangibly embodied in a carrier medium carrying machine-readable code for execution by a programmable processor. The present invention thus relates to a carrier medium carrying a computer program product that, when executed on computing means, provides instructions for executing any of the methods as described above. The term "carrier medium" refers to any medium that participates in providing instructions to a processor for execution. Such a medium may take many forms, including but not limited to, non-volatile media, and transmission media. Non-volatile media includes, for example, optical or magnetic disks, such as a storage device which is part of mass storage. Common forms of computer readable media include, a CD-ROM, a DVD, a flexible disk or floppy disk, a tape, a memory chip or cartridge or any other medium from which a computer can read. Various forms of computer readable media may be involved in carrying one or more sequences of one or more instructions to a processor for execution. The computer program product can also be transmitted via a carrier wave in a network, such as a LAN, a WAN or the Internet. Transmission media can take the form of acoustic or light waves, such as those generated during radio wave and infrared data communications. Transmission media include coaxial cables, copper wire and fibre optics, including the wires that comprise a bus within a computer.

Software according to the present invention, when executed on a processing engine is suitable for obtaining information about tooth movement caused by at least one orthodontic element fixed on a dentition, the software is adapted, when executed:

For receiving a digital model of a first dentition comprising teeth;

For determining of individual digitally modelled teeth of the first dentition and the type of digitally modelled teeth;

For digitally positioning at least one digitally modelled orthodontic element in the digital dentition model;

For identifying tooth axes and reference point;

For creation of desired tooth setup;

For selecting the at least one digitally modelled orthodontic element and positioning the at least one digitally modelled orthodontic element on a tooth and positioning at least one digitally modelled archwire;

For computing tooth loads generated by the digitally modelled archwire and resulting movement of the digitally modelled teeth.

The software is preferably also adapted, when executed, to compute tooth loads and movements comprises generating a first analytical model for modelling the at least one archwire and at least one orthodontic element to compute the forces and torques applied onto individual teeth.

The software is preferably also adapted, when executed, for inputting the computed forces and torques into a second analytical model representing the teeth and their periodontal ligament, and for computing induced tooth movements to form a second dentition.

The software is preferably also adapted, when executed, for verifying in the second dentition whether or not teeth make contact with or penetrate a neighbouring teeth.

The software is preferably also adapted, when executed, such that if teeth make contact, contact forces between neighbouring teeth are computed and taken into account as additional tooth load when computing a next tooth movement step.

The software is preferably also adapted, when executed, such that if a tooth penetrates into a neighbouring tooth, the tooth movement is limited until contact.

The software is preferably also adapted, when executed, to repeat calculation of forces and torques applied by the archwire, followed by calculating induced tooth movements, until the desired tooth setup is obtained.

The software is preferably also adapted, when executed, such that when calculated tooth movement is no longer induced by the applied loads, to allow replacement of the digitally modelled archwire by a stiffer archwire and repeating calculating forces and torques applied by the stiffer archwire, followed by calculating induced tooth movements, until the desired tooth setup is obtained.

The software is preferably also adapted, when executed, for tracking a treatment time to determine the total treatment time and/or points of time at which the archwire must be replaced with the next one.

The software is preferably also adapted, when executed, for repeating the calculations to determine for different archwires the tooth loads, the induced tooth movement, and the total treatment time and to allow selection of a set of archwire types.

The software is preferably also adapted, when executed, for repeating the calculations for different positions of the at least one orthodontic element and/or archwire shape.

The software is preferably also adapted, when executed, for repeating the calculations for different position of the reference point.

The present invention also includes storing the software on non-volatile media such as optical or magnetic disks, such as a storage device which is part of mass storage. Common forms of computer readable media include, a CD-ROM, a DVD, a flexible disk or floppy disk, a tape, a memory chip or cartridge or any other medium from which a computer can read.

Other arrangements for accomplishing the objectives of the device embodying the invention will be obvious for those skilled in the art.

The invention claimed is:

1. A computer based method for obtaining information about tooth movement caused by at least one orthodontic element fixed on a dentition, the method comprising the steps of:
   receiving a digital model of a first dentition comprising teeth;
   determining individual digitally modelled teeth of the first dentition and determining tooth types for the digitally modelled teeth;
   digitally positioning at least one digitally modelled orthodontic element in the digital dentition model;
   identifying tooth axes and a reference point;
   creating a desired tooth setup;
   selecting the at least one digitally modelled orthodontic element and positioning the at least one digitally modelled orthodontic element on a tooth and positioning at least one digitally modelled arch wire; and
   computing tooth loads generated by the digitally modelled archwire and resulting movement of the digitally modelled teeth.

2. The method of claim 1, wherein computing tooth loads and movements comprises generating a first analytical model for modelling the at least one archwire and at least one orthodontic element and computing the forces and torques applied onto individual teeth.

3. The method of claim 2, further comprising inputting the computed forces and torques into a second analytical model representing the teeth and their periodontal ligament, and computing induced tooth movements to form a second dentition.

4. The method according to claim 3, further comprising verifying in the second dentition whether or not teeth make contact with or penetrate a neighbouring tooth.

5. The method according to claim 4, wherein if teeth make contact, contact forces between neighbouring teeth are computed wherein said contact force is an additional tooth load used in computing a next tooth movement step.

6. The method according to claim 4, wherein if a tooth penetrates into a neighbouring tooth, the tooth movement is limited until contact.

7. The method according to claim 1, wherein the step of calculating forces and torques applied by the archwire, followed by calculating induced tooth movements, is repeated until the desired tooth setup is obtained.

8. The method of claim 1, wherein calculated tooth movement is no longer induced by the applied loads, replacement of the digitally modelled archwire by a stiffer archwire and the steps of calculating forces and torques applied by the archwire, followed by calculating induced tooth movements, are repeated until the desired tooth setup is obtained.

9. The method according to claim 1 further comprising tracking a treatment time to determine the total treatment time or points of time at which the archwire must be replaced with the next one.

10. The method according to claim 1, further comprising repeating the calculations to determine for different archwires the tooth loads, the induced tooth movement, and the total treatment time and selection of a set of archwire types; or further comprising repeating the calculations to determine for different positions of the at least one orthodontic element or archwire shape or at least one orthodontic element and archwire shape; or further comprising repeating the calculations for different positions of the reference point.

11. A computer based system for obtaining information about tooth movement caused by at least one orthodontic element fixed on a dentition, the system comprising:
   means for receiving a digital model of a first dentition comprising teeth;
   means for determining individual digitally modelled teeth of the first dentition and determining tooth types for the digitally modelled teeth;
   means for allowing digital positioning of at least one digitally modeled orthodontic element in the digital dentition model;
   means for allowing identification of tooth axes and a reference point;
   means for allowing creation of a desired tooth setup;
   means for selecting the at least one digitally modelled orthodontic element and positioning the at least one digitally modelled orthodontic element on a tooth and positioning at least one digitally modelled archwire; and
   means for computing tooth loads generated by the digitally modelled archwire and resulting movement of the digitally modelled teeth.

12. The system of claim 11, wherein the means for computing tooth loads and movements is adapted to generate a first analytical model for modelling the at least one archwire and at least one orthodontic element to compute the forces and torques applied onto individual teeth.

13. The system of claim 12, further comprising means for inputting the computed forces and torques into a second analytical model representing the teeth and their periodontal ligament, and means for computing induced tooth movements to form a second dentition.

14. The system according to claim 12, further comprising means for verifying in the second dentition whether or not teeth make contact with or penetrate a neighbouring tooth.

15. The system according to claim 14, wherein if teeth make contact, the system is adapted to compute contact forces between neighbouring teeth wherein said contact force is an additional tooth load used in computing a next tooth movement step.

16. The system according to claim 14, wherein if a tooth penetrates into a neighbouring tooth, the system is adapted to limit the tooth movement until contact.

17. The system according to claim 11, further comprising means for determining the total treatment time.

18. A computer program for generating, when executed, a method for obtaining information about tooth movement caused by at least one orthodontic element fixed on a dentition, the computer program being adapted to:
   receive a digital model of a first dentition comprising teeth;
   determine individual digitally modelled teeth of the first dentition and determine tooth types for the digitally modelled teeth;
   digitally position at least one digitally modelled orthodontic element in the digital dentition model;
   identify tooth axes and reference point;
   create desired tooth setup;
   select the at least one digitally modelled orthodontic element and positioning the at least one digitally modelled orthodontic element on a tooth and positioning at least one digitally modelled archwire; and
   compute tooth loads generated by the digitally modelled archwire and resulting movement of the digitally modelled teeth.

19. A non-transitory machine readable signal storage medium storing the computer program of claim 18.

\* \* \* \* \*